(12) United States Patent
Sevick-Muraca et al.

(10) Patent No.: US 7,865,230 B1
(45) Date of Patent: *Jan. 4, 2011

(54) METHOD AND SYSTEM FOR DETECTING SENTINEL LYMPH NODES

(75) Inventors: Eva M. Sevick-Muraca, College Station, TX (US); Michael Gurfinkel, Bryan, TX (US)

(73) Assignee: Texas A&M University System, College Station, TX (US)

( * ) Notice: Subject to any disclaimer, the term of this patent is extended or adjusted under 35 U.S.C. 154(b) by 2046 days.

This patent is subject to a terminal disclaimer.

(21) Appl. No.: 10/618,194

(22) Filed: Jul. 11, 2003

Related U.S. Application Data

(63) Continuation-in-part of application No. 09/870,144, filed on May 30, 2001, now Pat. No. 7,328,059, which is a continuation of application No. 09/367,148, filed as application No. PCT/US98/02354 on Feb. 6, 1998, now abandoned.

(60) Provisional application No. 60/039,318, filed on Feb. 7, 1997.

(51) Int. Cl.
*A61B 5/00* (2006.01)
(52) U.S. Cl. ....................... 600/473; 600/476
(58) Field of Classification Search .......... 600/476–480
See application file for complete search history.

(56) References Cited

U.S. PATENT DOCUMENTS

| | | | |
|---|---|---|---|
| 4,541,438 A | 9/1985 | Parker et al. ............... 128/664 |
| 5,022,757 A | 6/1991 | Modell ....................... 128/664 |
| 5,119,815 A | 6/1992 | Chance ...................... 128/633 |
| 5,142,372 A | 8/1992 | Alfano et al. ............... 128/664 |
| 5,190,729 A | 3/1993 | Hauenstein et al. | |
| 5,208,651 A | 5/1993 | Buican ....................... 356/346 |
| 5,213,105 A * | 5/1993 | Gratton et al. .............. 600/473 |
| 5,340,991 A | 8/1994 | Fransen et al. ............. 128/664 |
| 5,353,799 A * | 10/1994 | Chance ....................... 600/473 |
| 5,413,098 A | 5/1995 | Benaron ..................... 128/633 |
| 5,421,337 A | 6/1995 | Richards-Kortum et al. 128/633 |

(Continued)

FOREIGN PATENT DOCUMENTS

EP 0 959 341 A1 5/1999

(Continued)

OTHER PUBLICATIONS

M.A. O'Leary, E.A. Boas, X.D. Li, B. Chance, and A.G. Yodh., "*Fluorescence Lifetime Imaging in Turbid Media*," Optics Letters, vol. 21, No. 2, pp. 158-160,) Jan. 15, 1996.

(Continued)

*Primary Examiner*—Eric F Winakur
(74) *Attorney, Agent, or Firm*—Conley Rose, P.C.

(57) ABSTRACT

According to one embodiment of the present invention, a method for detecting lymph nodes in a human includes introducing a fluorescent contrast agent into a lymph node system of a body, directing near-infrared time-varying excitation light into the tissue of the body, causing the near-infrared time-varying excitation light to contact a lymph node of the lymphatic system, whereby a redshifted and time-varying emission light is generated, detecting the time-varying emission light at a surface of the body, filtering the time-varying emission light to reject excitation light re-emitted from the lymph node, and imaging the lymph node of the lymphatic system.

23 Claims, 7 Drawing Sheets

U.S. PATENT DOCUMENTS

| | | | |
|---|---|---|---|
| 5,421,339 A | 6/1995 | Ramanujam et al. | 128/665 |
| 5,424,843 A | 6/1995 | Tromberg et al. | 356/442 |
| 5,441,054 A * | 8/1995 | Tsuchiya | 600/310 |
| 5,452,723 A | 9/1995 | Wu et al. | 128/665 |
| 5,485,530 A | 1/1996 | Lakowicz et al. | 382/191 |
| 5,504,337 A | 4/1996 | Lakowicz et al. | 250/461.2 |
| 5,507,287 A | 4/1996 | Palcic et al. | 128/633 |
| 5,579,773 A | 12/1996 | Vo-Dinh et al. | 128/665 |
| 5,582,168 A | 12/1996 | Samuels et al. | 128/633 |
| 5,590,660 A | 1/1997 | MacAulay et al. | 128/664 |
| 5,624,847 A | 4/1997 | Lakowicz et al. | 436/68 |
| 5,628,310 A | 5/1997 | Rao et al. | 600/317 |
| 5,647,368 A | 7/1997 | Zeng et al. | 128/665 |
| 5,673,701 A * | 10/1997 | Chance | 600/473 |
| 5,692,504 A | 12/1997 | Essenpreis et al. | 600/316 |
| 5,699,798 A * | 12/1997 | Hochman et al. | 600/420 |
| 5,736,410 A | 4/1998 | Zarling et al. | |
| 5,759,767 A | 6/1998 | Lakowicz et al. | 435/4 |
| 5,792,049 A | 8/1998 | Eppstein et al. | 600/306 |
| 5,818,583 A | 10/1998 | Sevick-Muraca et al. | 356/336 |
| 5,832,931 A | 11/1998 | Wachter et al. | 128/898 |
| 5,860,421 A | 1/1999 | Eppstein et al. | 128/660.06 |
| 5,865,754 A | 2/1999 | Sevick-Muraca et al. | 600/476 |
| 5,891,656 A | 4/1999 | Zarling et al. | 435/7.92 |
| 5,917,190 A | 6/1999 | Yodh et al. | 250/458.1 |
| 5,919,140 A | 7/1999 | Perelman et al. | 600/476 |
| 5,928,627 A | 7/1999 | Kiefer et al. | 424/9.6 |
| 5,949,077 A | 9/1999 | Alfano et al. | 250/459.1 |
| 5,987,346 A * | 11/1999 | Benaron et al. | 600/407 |
| 6,070,583 A | 6/2000 | Perelman et al. | 600/600 |
| 6,216,540 B1 | 4/2001 | Nelson et al. | 73/633 |
| 6,271,522 B1 | 8/2001 | Lindermeir et al. | 250/341.1 |
| 6,304,771 B1 | 10/2001 | Yodh et al. | 600/476 |
| 6,321,111 B1 | 11/2001 | Perelman et al. | 600/477 |
| 6,480,276 B1 | 11/2002 | Jiang | 356/336 |
| 6,671,540 B1 | 12/2003 | Hochman | 600/431 |
| 6,804,549 B2 * | 10/2004 | Hayashi | 600/431 |
| 7,054,002 B1 | 5/2006 | Sevick-Muraca et al. | 356/317 |
| 2003/0117622 A1 | 6/2003 | Sevick-Muraca et al. | |
| 2005/0073681 A1 | 4/2005 | Sevick-Muraca et al. | |

FOREIGN PATENT DOCUMENTS

| | | |
|---|---|---|
| GB | 2311366 A | 3/1996 |
| JP | 2-268256 | 1/1990 |
| JP | H07-507472 | 8/1995 |
| WO | WO 95/12132 | 5/1995 |
| WO | WO 97/08538 | 3/1997 |
| WO | WO 99/49312 | 3/1999 |
| WO | WO 00/22414 | 10/1999 |
| WO | WO 01/22063 A1 | 9/2000 |
| WO | WO 02/41760 A2 | 5/2002 |

OTHER PUBLICATIONS

Reynolds, et al., "*Imaging of Spontaneous Canine Mammary Tumors Using Fluorescent Contrast Agents*", Photochemistry and Photobiology, 1999: 70(1): 87-94 (XP-001063376), Apr. 14, 1999.

Gurfinkel, et al., "*Pharmacokinetcs of ICG and HPPH-car for the Detection of Normal and Tumor Tissue Using Fluorescence, Near-infrared Reflectance Imaging: A Case Study*", Photochemistry and Photobiology, 2000: 72(1): 94-102 (XP-001030699), Apr. 28, 2000.

Thompson, et al., "*Near-infrared fluorescence contrast-enhanced imaging with intensified charge-coupled device homodyne detection: measurement precision and accuracy*", Journal of Biomedical Optics, 2003: 8(1): 111-120 (XP-002301882), Jan. 2003.

Thompson, et al., "*Near-infrared fluorescence contrast-enhanced imaging with area illumination and area detection: the forward imaging problem*", Applied Optics, 2003: 42(19): 4125-4136 (XP-002301883), Jul. 1, 2003.

Notification of Transmittal of the International Search Report and the Written Opinion of the International Searching Authority for International Application No. PCT/US2004/019792, filed Jun. 18, 2004 (14 pages), Nov. 8, 2004.

Reynolds et al., "*Imaging of Spontaneous Canine Mammary Tumors Using Fluorescent Contrast Agents*," Photochemistry and Photobiology, 1999, vol. 70(1), pp. 87-94.

Houston, et al., "*Sensitivity and Depth Penetration of Continuous Wave Versus Frequency-domain Photon Migration Near-infrared Fluorescence Contrast-enhanced Imaging*," Photochemistry and Photobiology, 2003, vol. 77(4), pp. 420-430.

Ntziachristos, et al. "*In Vivo Tomographic Imaging of Near-Infrared Fluorescent Probes*," Molecular Imaging, vol. 1(2), Apr. 2002, pp. 82-88.

U.S. Appl. No. 10/115,271, filed Apr. 3, 2002, entitled "*Method For Characterizing Particles in Suspension From Frequency Domain Photon Migration Measurements*", currently pending.

PCT Patent Application No. PCT/US99/23709 filed Oct. 8, 1999, entitled "*Characterization of Luminescence in a Scattering Medium*," currently pending.

Sevick-Muraca, et al.; *Method for Characterizing Particles in Suspension from Frequency Domain Photon Migration Measurements*; U.S. Appl. No. 11/204,844; 59 pgs. (Abandoned), Aug. 16, 2005.

E. M. Sevick et al., "*Localization of absorber in Scattering Media by use of frequency-domain measurements of time-dependent photon migration*", Applied Optics, vol. 33 No. 16, pp. 3562-03570, Jun. 1994.

Richard Haskel et al., "*Boundary conditions for the diffusion equation in radiative transfer*", J. Opt. Soc. Am., A. vol. 11, No. 10, pp. 2727-2741, Oct. 1994.

R. L. Sheridan et al., "*Burn depth estimation by use of indocyanine green fluorescence: Initial human trial*", Journal of Burn Care & Rehabilitation, vol. 16 No. 4, pp. 1-5.

Huabei Jiang et al., "*Optics image reconstruction using frequency-domain data; simulations and experiments*", J. Opt. Soc. Am., vol. 13, No. 2, pp. 253-266, Feb. 1996.

Alwin Dienle et al., "*Spatially resolved absolute diffuse refletance measurements for noninvasive determination of the optical scattering and absorption coefficients of biological tissue*", Applied Optics, vol. 35, No. 13, pp. 2304-2314, May 1996.

X. D. Li et al., "*Fluorescent diffuse photon density waves in homogenous and heterogeneous turbid media; analytic solutions and applications*", Applied Optics, vol. 35, No. 19, pp. 3746-3758, Jul. 1996.

Michael Patterson et al., "*Applications of time-resolved light scattering measurements to photodynamic therapy dosimetry*", Applied Optics 1203-1208.

Michael Patterson et al., "*Diffusion equation representation of photon migration in tissue*".

Eva Sevick-Muraca et al., "*Origin of phosphorescence signals reemitted from tissues*", Optics Letters, vol. 19, No. 23, pp. 1928-1930, Dec. 1994.

Christina Hutchinson et al., "*Fluorescence lifetime-based sensing in tissues: a computational study*", Biophysical Journal, vol. 68, pp. 1574-1584, Apr. 1995.

B. W. Pogue et al., "*Initial Assessment of a simple system for frequency domain diffuse optical tomography*", Phys. Med. Biol. 40, (1995) 1709-1729.

Stefan Anderson-Engels et al., "*Laser induced fluorescence in malignant and normal tissue of rats injected with benzoporphyrin derivative*", Photochemistry and Photobiology, vol. 57, No. 6, pp. 978-983, 1993.

Jun Wun et al., "*Three-dimensional imaging of objects embedded in turbid media with fluorescence and raman spectroscopy*", Applied Optics, vol. 34, No. 18, pp. 3425-3430, Jun. 1995.

Scott R. Fulton, et al., "*Time-resolved laser-induced fluorescence spectroscopy for enhanced demarcation of human atherosclerotic plaques*", Journal of Photochemistry and Photobiology, (1990) pp. 363-369.

Seth Fraden et al., "*Multiple light scattering from concentrated, interacting suspensions*", Physical Review letters, vol. 65, No. 4, pp. 512-515.

K. M. Yoo et al., "*Imaging objects hidden in scattering media using a fluorescence-absorption technique*", Optics Letters, vol. 16, No. 16, pp. 1252-1254, 1991.

R. C. Straight et al., "*Application of Charge-coupled device technology for measurement of laser light and fluorescence distribution in tumors for photodynamic therapy*", Photochemistry and Photobiology, vol. 53, No. 6, pp. 787-796.

E. M. Sevick et al., "*Frequency domain imaging absorbers obscured by scattering*", J. Photochem, Photobiol. B:Biol, 16 (1992) pp. 169-185.

Wai S. Poon et al., "*Laser-induced Fluorescence Experimental intraoperative delineation of tumor resection margins*", J. Neurosurg, vol. 76, pp. 679-686, Apr. 1992.

Brian C. Wilson et al., "*Time-dependent optical spectroscopy and imaging for biomedical applications*", Proceedings of the IEEE, vol. 80, No. 6, pp. 918-930, Jun. 1992.

A. Knuittel et al., "*Acoust-optic scanning and interfering photon density waves for precise localization of an absorbing (or fluorescence) body in a turbid medium*", Rev. Sci. Instrum. vol. 64, No. 3, pp. 638-644, Mar. 1993.

R. Cubeddu et al., "*Time-gated Fluorescence imaging for the diagnosis of tumors in a murine model*", Photochemistry and Photobiology, vol. 57, No. 3, pp. 480-485.

Randall Barbour et al., "*A perturbation approach for optical diffusion tomography using continuous-wave and time-resolved data*", Medical Optical Tomography, pp. 87-121.

M. A. O'Leary et al., "*Reradiation and imaging of diffuse photon density waves using fluorescent inhomogeneities*", Journal of Luminescence, (1994) pp. 281-286.

Michael S. Patterson et al., "*Mathematical model for time-resolved and frequency-domain fluorescence spectroscopy in biologocal tissues*", Applied Optics, vol. 33, No. 10, pp. 1963-1974, Apr. 1994.

David A. Russel et al., "*Continuous noninvasive measurement of In Vivo pH in conscious mice*", Photochemistry and Photobiology, vol. 59, No. 3 (1994) pp. 309-313.

Serge Mordon et al., "*In Vivo pH measurement and imaging of tumor tissue using a pH-sensitive fluorescent probe (5,6-carboxyfluorescein): Instrumental and Experimental studies*", Photochemistry and Photobiology, vol. 60, No. 3, pp. 274-279.

Jun Wu et al., "*Time-resolved multichannel imaging off luorescent objects embedded in turbid media*", Optic Letters, vol. 20, No. 5, pp. 489-491, Mar. 1995.

Grafton, et al., *A Continuously Variable Frequency Cross-Correlation Phase Fluorometer with Picosecond Resolution*, © Biophysical Society, Biophysical Journal, vol. 44, pp. 315-324, Dec. 1983.

Grafton, et al., *The possibility of a near-infrared optical imaging system using frequency domain method*, Mind Brain Imaging Program, Hamamatsu, Japan, pp. 183-189, Aug. 5-Oct. 1990.

Sevick, et al., *Quantitation of Time-and Frequency-Resolved Optical Spectra for the Determination of Tissue Oxygenation*, Analytical Biochemistry 195, © 1991 Academic Press Inc., pp. 330-351.

Fishkin, et al., *Propagation of photon-density waves in strongly scattering media containing an absorbing semi-infinite plane bounded by a straight edge*, vol. 10, No. 1, © 1993 Optical Society of America, pp. 127-140, Jan. 1993.

Tromberg, et al., *Properties of photon density waves in multiple-scattering media*, vol. 32, No. 4, Applied Optics, pp. 607-616, Feb. 1, 1993.

Madsen, et al., *Determination of the optical properties of the human uterus using frequency-domain photon migration and steady-state techniques*, Phys. Med. Biol. 39, © 1994 IOP Publishing Ltd., pp. 1191-1202.

Fantini, et al., *Quantitative determination of the absorption spectra of chromophores in strongly scattering media: a light-emitting diode based technique*, Applied Optics, vol. 33, No. 22, pp. 52045213, Aug. 1, 1994.

Fishkin, et al., *Frequency-domain method for measuring spectral properties in multiple-scattering media: methemoglobin absorption spectrum in a tissuelike phantom*, Applied Optics, vol. 34, No. 7, pp. 1143-1155, Mar. 1, 1995.

Pham, et al., *Broad bandwidth frequency domain instrument for quantitative tissue optical spectroscopy*, Review of Scientific Instruments, vol. 71, No. 6, © 2000 American Institute of Physics, pp. 2500-2513, Jun. 2000.

Hawrysz, et al., *Developments Toward Diagnostic Breast Cancer Imaging Using Near-Infrared Optical Measurements and Fluorescent Contrast Agents'*, Review Article, Neoplasia, vol. 2, No. 5, © 2000 Nature America, Inc., pp. 388-417, Sep.-Oct. 2000.

Tromberg, et al., *Non-invasive measurements of breast tissue optical properties using frequency-domain photon migration*, Phil. Trans. R. Soc. Lond. B, © 1997 The Royal Society, pp. 661-668.

Muzzio, et al., *Sampling practices in powder blending*, Research papers, International Journal of Pharmaceutics 155, © 1997 Elsevier Science RV, pp. 153-178.

Fishkin, et al., *Frequency-domain photon migration measurements of normal and malignant tissue optical properties in a human subject*, Applied Optics, vol. 36, No. 1, pp. 10-20, Jan. 1, 1997.

Sevick-Muraca, et al., *Photon-Migration Measurement of Latex Size Distribution in Concentrated Suspensions*, Particle Technology and Fluidization, AIChE Journal, vol. 43, No. 3, pp. 655-664, Mar. 1997.

Richter, et al., *Particle Sizing Using Frequency Domain Photon Migration*, Part. Part. Syst. Charact. 15, © Wiley-VCH Verlag GmbH, D-69469 Weinheim, pp. 9-15, 1998.

Ramanujam, et al., *Sources of phase noise in homodyne and heterodyne phase modulation devices used for tissue oximetry studies*, Review of Scientific Instruments, vol. 69, No. 8, © 1998 American Institute of Physics, pp. 3042-3054, Aug. 1998.

Chance, et al., Review Article, *Phase measurement of light absorption and scatter in human tissue*, Review of Scientific Instruments, vol. 69, No. 10, © 1998 American Institute of Physics, pp. 34573481, Oct. 1998.

Banerjee, et al.; *Probing Static Structure of Colloid-Polymer Suspensions with Multiply Scattered Light*, Journal of Colloid and Interface Science 209, © 1999 by Academic Press, pp. 142-153.

Shinde, et al., *Investigation of static structure factor in dense suspensions by use of multiply scattered light*, Applied Optics, vol. 38, No. 1, © 1999 Optical Society of America, pp. 197-204, Jan. 1, 1999.

Gerken, et al., *High-precision frequency-domain measurements of the optical properties of turbid media*, Optics Letters, vol. 24, No. 14, © 1999 Optical Society of America, pp. 930-932, Jul. 15, 1999.

Shinde, et al., *Frequency-Domain Photon Migration Measurements for Quantitative Assessment of Powder Absorbance: A Novel Sensor of Blend Homogeneity*, Research Articles, © 1999 American Chemical Society and American Pharmaceutical Association, Journal of Pharmaceutical Sciences, vol. 88, No. 10, pp. 959-966, Oct. 1999.

Banerjee, et al., *Assessment, of S(0,0) from multiply scattered light*, Journal of Chemical Physics, vol. 111, No. 20, © 1999 American Institute of Physics, pp. 9133-9136, Nov. 22, 1999.

Sun, et al., "*Particle Characterization of Colloidal Suspension at High Volume Fractions Using Frequency Domain Photon Migration,*" 6th World Congress of Chemical Engineering, Melbourne 2001, pp. 4/15-12/15.

Sun, et al., "*Inversion Algorithms for Particle Sizing with Photon Migration Measurements,*" Fluid Mechanics and Transport Phenomena, A1ChE Journal, vol. 47, No. 7, pp. 1487-1498, Jul. 2001.

Hutchinson, Christina L., et al., "*Fluorescence-Lifetime Determination in Tissues or Other Scattering Media from Measurement of Excitation and Emission Kinetics*", Applied Optics, vol. 35, No. 13, pp. 2325-2332, May 1, 1996.

Sun, et al., "*Approach for Particle Sizing in Dense Polydisperse Colloidal Suspension Using Multiple Scattered Light,*" XP-001126299, Langmuir 2001, 17, 2001 American Chemical Society, pp. 6142-6147, Sep. 8, 2001.

Isayev, K, et al., "*Study of Thermophysical Properties of a Metal-Hydrogen System,*" International Journal of Hydrogen Energy, vol. 21, No. 11-12, pp. 1129-1132, Nov. 12, 1996.

Panda, et al., "*Generalized B-Spline Signal Processing,*" European Journal Devoted to the Methods and Applications of Signal Processing, Elsevier Science Publishers, B.V. Amsterdam, NL, vol. 55, No. 1, XP004016005, pp. 1-14, Nov. 1, 1996.

PCT Invitation to Pay Additional Fees (PCT Article 17(3)(a) and Rule 40.1), Annex to Form PCT/ISA/206 Communication Regarding to the Results of the Partial International Search Authority, regarding PCT/US02/10433, filed Apr. 3, 2002, Applicant's reference 017575.0748, 6 pages, Nov. 29, 2002.

PCT International Search Report in International Application No. 02/10433, 10 pages, Jun. 16, 2003.

Pan, et al., *Volume of Pharmaceutical Powders Probed by Frequency-Domain Photon Migration Measurements of Multiply Scattered Light*, Analytical Chemistry 2002, vol. 74, No. 16, © 2002 American Chemical Society, pp. 4228-4234, Aug. 15, 2002.

Richter, et al., *Characterization of concentrated colloidal suspensions using time-dependent photon migration measurements*, Reprinted from Colloids And Surfaces An International Journal, A: Physicochemical and Engineering Aspects, © 2000 Elsevier Science RV, pp. 163-173, plus cover.

Mayer, Ralf H., et al., "*Measurement of the Fluorescence Lifetime in Scattering Media by Frequency-Domain Photon Migration*", Applied Optics, vol. 38, No. 22, pp. 4930-4938, Aug. 1, 1999.

Cerussi, Albert E., et al., "*Experimental Verification of a Theory for the Time-Resolved Fluorescence Spectroscopy of Thick Tissues*", Applied Optics, vol. 36, No. 1, pp. 116-124, Jan. 1, 1997.

Correspondence regarding Application No. 04 755 747.5—1234, Reference No. JL5973, Communication Pursuant to Article 94(3) EPC received from EPO, Examiner Erik Verdoodt, dated Nov. 13, 2009.

\* cited by examiner

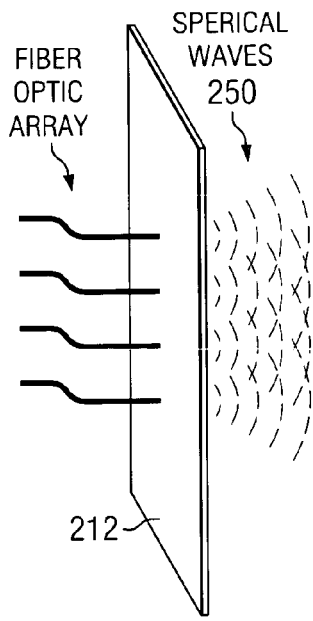
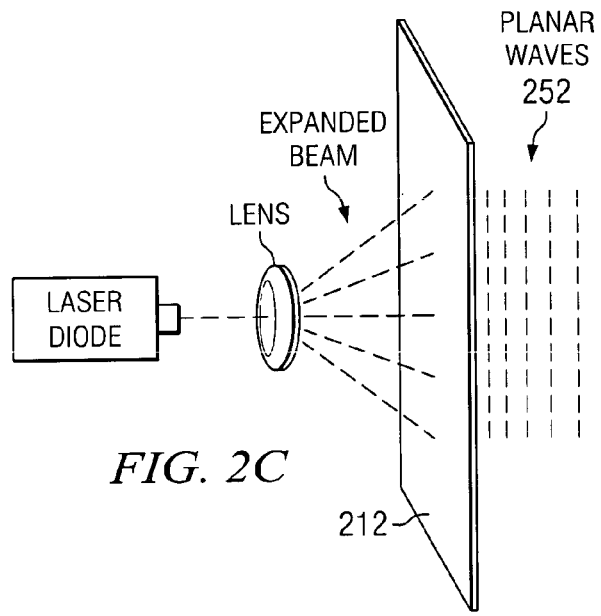
*FIG. 2B*
*FIG. 2C*
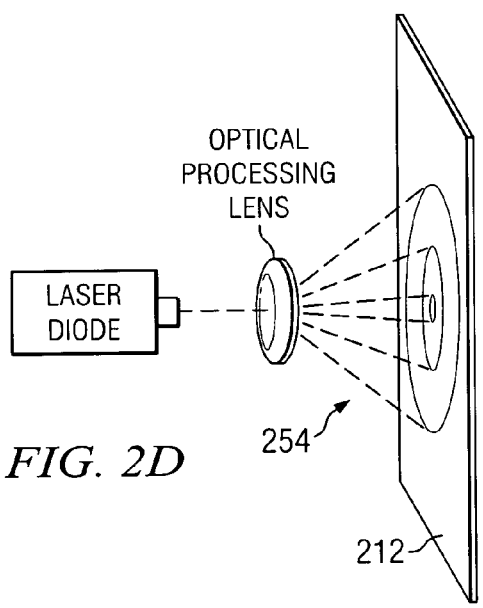
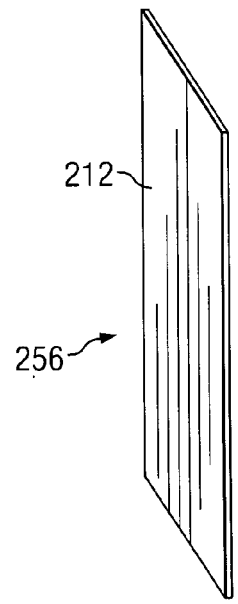
*FIG. 2D*
*FIG. 2E*

AC [a.u.] ICG target at 2cm

DC (a.u.) NO TARGET

AC (a.u.) NO TARGET

METHOD AND SYSTEM FOR DETECTING SENTINEL LYMPH NODES

RELATED APPLICATIONS

This application claims the benefit of Ser. No. 60/395,279, entitled "Detecting Sentinel Lymph Nodes," filed provisionally on Jul. 12, 2002.

This application also claims the benefit of Ser. No. 60/480,526 entitled "Method and System for Near-Infrared Fluorescence Contrast-Enhanced Imaging with Area Illumination and Area Detection," filed provisionally on Jun. 20, 2003.

This application is also a continuation-in-part of U.S. application Ser. No. 09/870,144, filed May 30, 2001, now U.S. Pat. No. 7,328,059 and entitled "Imaging of Light Scattering Tissues with Fluorescent Contrast Agents," now pending, which is a continuation of U.S. application Ser. No. 09/367,148, filed Nov. 22, 1999, now abandoned, which was the National Stage of International Application No. PCT/US/98/02354, filed Feb. 6, 1998, which claims the benefit of U.S. Provisional Application No. 60/039,318, filed Feb. 7, 1997.

GOVERNMENT RIGHTS

This invention was made with Government support from the National Institute of Health, Contract Nos. R01 CA67176 and R21 CA 96305-01. The government may have certain rights in this invention.

TECHNICAL FIELD OF THE INVENTION

This invention relates generally to the field of medical imaging and, more specifically, to a method and system for detecting sentinel lymph nodes for surgical resection and prognostic indication of cancer spread through lymph flow.

BACKGROUND OF THE INVENTION

The status of the lymph nodes serves as the most important prognostic indicators for patients with breast carcinoma and provides one of the parameters that indicates the need for adjuvant treatment. Breast cancer patients with mammographically detected cancers first undergo diagnostic lymphoscintigraphy. Lymphoscintigraphy is typically performed using a radiocolloid as a nonspecific contrast agent injected peritumorally for nuclear imaging and localization of sentinel or closest lymph nodes for surgical resection and subsequent biopsy. The resection and biopsy of the sentinel rather than major lymph nodes minimize surgical evasiveness.

However, in breast cancer patients, lymphoscintigraphy is compromised by increased amounts of adipose tissue in obese subjects, where the sentinel lymph location can be as deep as 4 cm from the tissue surface. Nuclear imaging is also hampered by chemotherapy, which may shrink the size of the lymph node to as small as 5 mm. In addition, nuclear imaging may not provide adequate sentinel node detection because of slow and inconsistent drainage of radiopharmaceuticals through the lymphatic system.

U.S. Pat. No. 5,865,754 to Sevick-Muraca et al. describes a fluorescence imaging system that relates to in vivo imaging of biologic tissue by mapping a fluorescence characteristic of the tissue through the detection of light emitted in response to excitation light from a time-varying light source.

SUMMARY OF THE INVENTION

According to one embodiment of the present invention, a method for detecting lymph nodes in a human includes introducing a fluorescent contrast agent into a lymph node system of a body, directing near-infrared time-varying excitation light into the tissue of the body, causing the near-infrared time-varying excitation light to contact a lymph node of the lymphatic system, whereby a redshifted and time-varying emission light is generated, detecting the time-varying emission light at a surface of the body, filtering the time-varying emission light to reject excitation light re-emitted from the lymph node, and imaging the lymph node of the lymphatic system. Embodiments of the invention provide a number of technical advantages.

Embodiments of the invention may include all, some, or none of these advantages. In one embodiment, fluorescence-enhanced near-infrared optical imaging measurements provide localization of small targets at substantial tissue depths. This leads to the utilization of nonradioactive tracers for the management of cancer and other diseases, which eliminates the need for potentially harmful nuclear imaging methods that employ ionizing radiation. Fluorescent contrast agents may be used to provide signals for localization of sentinel lymph nodes and, depending on the type of contrast agent, may provide an assessment of lymph node status (i.e., whether or not cancer cells are present), thereby eliminating the need for surgical resection.

Other technical advantages are readily apparent to one skilled in the art from the following figures, descriptions, and claims.

BRIEF DESCRIPTION OF THE DRAWINGS

For a more complete understanding of the present invention and its features and advantages, reference is now made to the following description, taken in conjunction with the accompanying drawings, in which:

FIGS. 2B through 2E are schematics similar to FIG. 2A illustrating the propagation of other types of excitation waves;

DETAILED DESCRIPTION OF THE DRAWINGS

Figure 1:
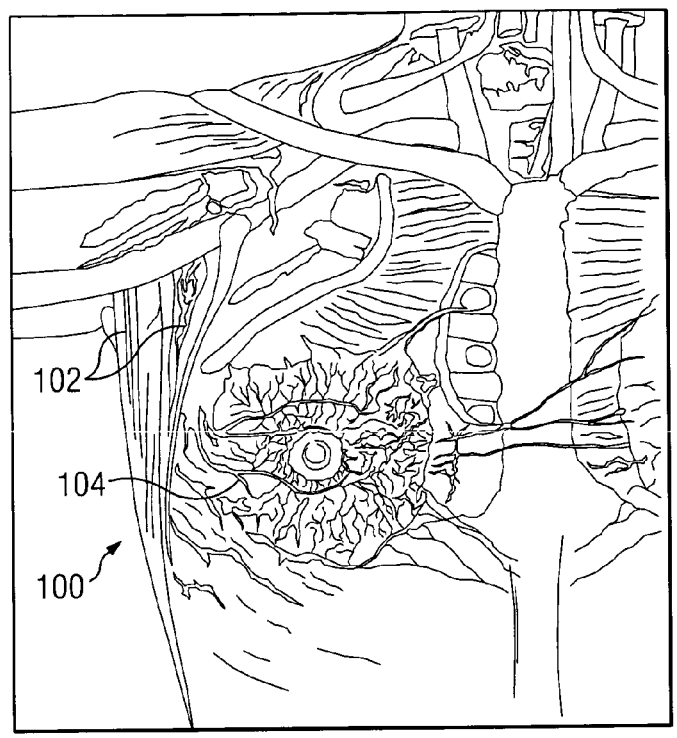
FIG. 1 is a schematic depicting lymphatic structure near a breast of a human.

FIG. 1 is a schematic of a lymphatic structure near a breast 100 of a human. The use of a less invasive sentinel lymph node biopsy to stage the status of the axillary lymph nodes 102 is desirable for health and safety reasons. Sentinel lymph node biopsy involves removing the sentinel lymph node, which is the first node to which a primary tumor drains before draining into the major node, such as the axillary or internal mammary lymph nodes (as denoted by reference numeral 104). Since lymphatic dissemination of breast carcinoma occurs in a stepwise fashion, the sentinel node is thought to be the first lymph node in which metastasis can be found. If no metastases are found in the sentinel lymph node, it is likely that no metastases are present in the remaining axillary and internal mammary lymph nodes to which it drains. Negative predictive values of greater than 95% have been obtained with sentinel lymph node biopsies. Furthermore, researchers have demonstrated that the status of sentinel lymph node accurately predicts the metastatic status of the remaining axillary nodes with positive predictive values of 100%. Thus, a sentinel lymph node biopsy may obviate unnecessary extensive dissection of the axillary lymph node basin in over half of all patients.

Currently, there are two main methods used to detect the sentinel lymph node: (1) lymphoscintigraphy and (ii) sentinel lymph node mapping. In lymphoscintigraphy, a radiocolloid, generally technetium-99m, is injected peritumorally and the breast is massaged. The tracer slowly is taken up by the lymph and transits to the sentinel node and then to the axillary or internal mammary nodes. During this time, the gamma emission given off by the technetium colloid is collected to provide a gamma image providing a gross location of the draining lymph nodes. The second approach is termed sentinel lymph node mapping. In this procedure performed interoperatively, the sentinel lymph node is detected intraoperatively either visually after the injection of blue dye (isosulfan blue) at the site of the primary tumor or by nuclear imaging or scanning with a handheld gamma probe following injection of a radiopharmaceutical, such as technetium-99m sulfur colloid. Both methods of administering the radiopharmaceutical and the isosulfan blue dye can be used independently or concurrently with success rates varying between 80%-95%. The success rate at any particular institution, however, is highly dependent upon the surgeons' experience. In addition, the localization of the sentinel node is more difficult and less successful in patients with fatty tissue as well as those undergoing adjuvant therapy. In the latter case, the lymph nodes can be significantly shrunken, and more difficult to localize.

According to the teachings of one embodiment of the present invention, near-infrared ("NW") frequency-domain photon migration ("FPDM") imaging techniques coupled with fluorescent contrast agents facilitates imaging and localization of the sentinel lymph nodes. Other suitable imaging techniques may be utilized for imaging of lymph nodes, such as magnetic resonance imaging using, among other suitable agents, iron oxide contrast agents; or ultrasound using microbubble emulsions.

However, unlike these conventional techniques that require tissue concentrations of exogenous contrast agents at millimolar concentrations, both nuclear and fluorescence optical imaging techniques require orders of magnitude lower tissue concentrations to generate images. This enables the opportunity for molecularly targeted fluorescent contrast agents that specifically bind to cancer cells within the lymphatic system. Specificity is achieved by chemically conjugating the fluorescent molecule to a ligand that specifically binds to an overexpressed receptor or is acted upon enzymes specific to the cancer cells. The use of fluorescence agents for imaging for sentinel lymph node is accomplished using imaging techniques such as those techniques described in U.S. Pat. No. 5,865,754, which is herein incorporated by reference for all purposes. In another embodiment, when these molecularly targeting fluorescent agents are conjugated with suitable targeting peptides or polymers with enzyme-specific cleavage sites that are specific to molecular markers of cancer, fluorescent signals provide an assessment of lymph node status in situ, thereby eliminating the need for dangerous surgical resection.

It should be noted that the use of fluorescent agents is not limited to imaging the lymphatic drainage of the breast, but may be used for cases of melanoma, colon cancer, and an increasing number of solid tumor cancers, among others.

Figure 2A:
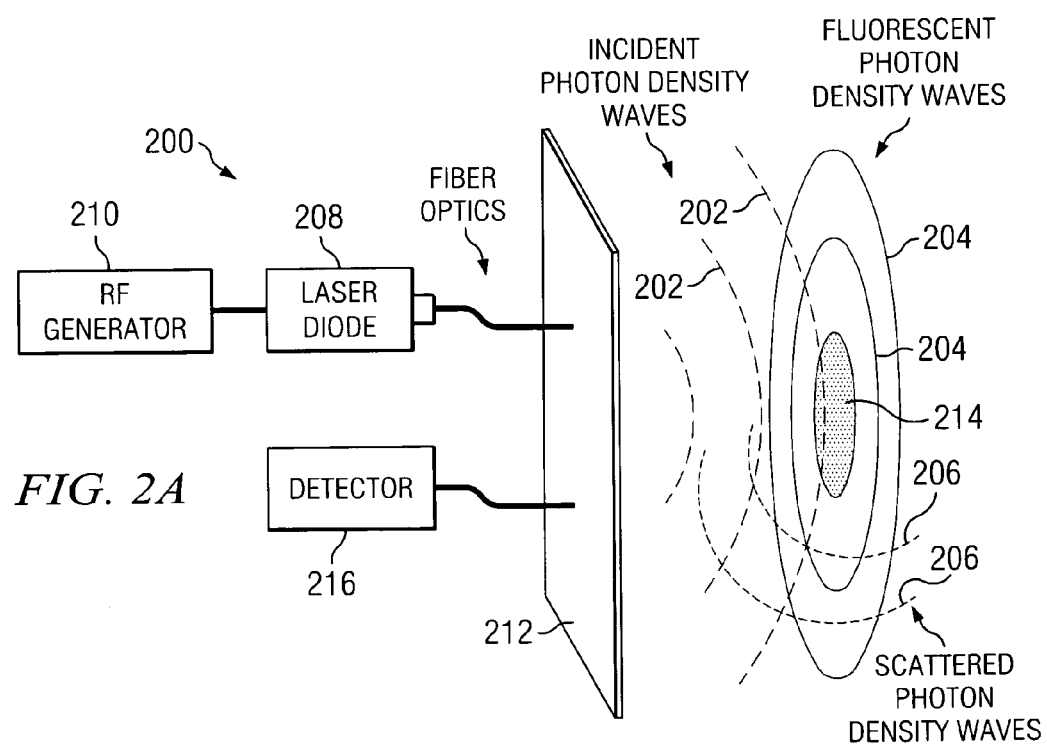
FIG. 2A is a schematic illustrating a frequency-domain photon migration system and resulting propagation of a spherical excitation wave and the generated emission wave, as well as the scattered excitation wave.

FIG. 2A is a schematic of an FPDM system 200 illustrating the propagation of a spherical excitation wave 202 and a generated emission wave 204, as well as a scattered excitation wave 206. Briefly, FDPM involves launching spherical excitation wave 202 of near-infrared ("NIR") light from one or more laser diodes 208 into the tissue of a body of interest. In other embodiments, excitation wave 202 may be an array of spherical waves that illuminate the tissue boundary, as denoted by reference numeral 250 in FIG. 2B, planar (area) waves from an expanded beam of light, as denoted by reference numeral 252 in FIG. 2C, spherical distributions of concentric circles, as denoted by reference numeral 254 in FIG. 2D, or a ronchi rule pattern, as denoted by reference numeral 256 in FIG. 2E. Excitation wave 202 may be intensity-modulated as produced by a frequency generator 210 driving laser diode 208 or other suitable NIR light source. Since NIR light of approximately 700-900 nm wavelength can penetrate several centimeters of tissue without the harmful radiation effects of gamma rays, x-rays, or ultraviolet light, it is advantageous for biomedical imaging and may be used to image as deep as five centimeters or more beneath a surface 212 of the tissue.

Various techniques for NIR fluorescence contrast-enhanced imaging with area illumination and area detection are also illustrated in U.S. Provisional Patent Application No. 60/480,526, filed Jun. 20, 2003, which is herein incorporated by reference for all purposes.

As shown in FIG. 2A, NIR excitation wave 202 propagates through the tissue and towards a target body 214, such as a lymph node. When excitation wave 202 contacts target body 214, which has been enhanced by a suitable fluorescent contrast agent, as described in greater detail below, excitation wave 202 causes generated red-shifted emission wave 204, as well as scattered fluorescent wave 206. Emission wave 204 then propagates towards surface 212 and is detected by a detector 216 as it exits surface 212. Detector 216 may be any suitable detector, such as an intensified charge coupled device ("CCD") camera, photon multiplier tube, or photodiode capable of detecting the intensity modulated fluorescent light. Target body 214 is then imaged in any suitable manner. Examples of such imaging techniques are aptly described in U.S. Pat. No. 5,865,754. An example FPDM imaging technique is described with reference to the flowchart of FIG. 3.

Figure 3:
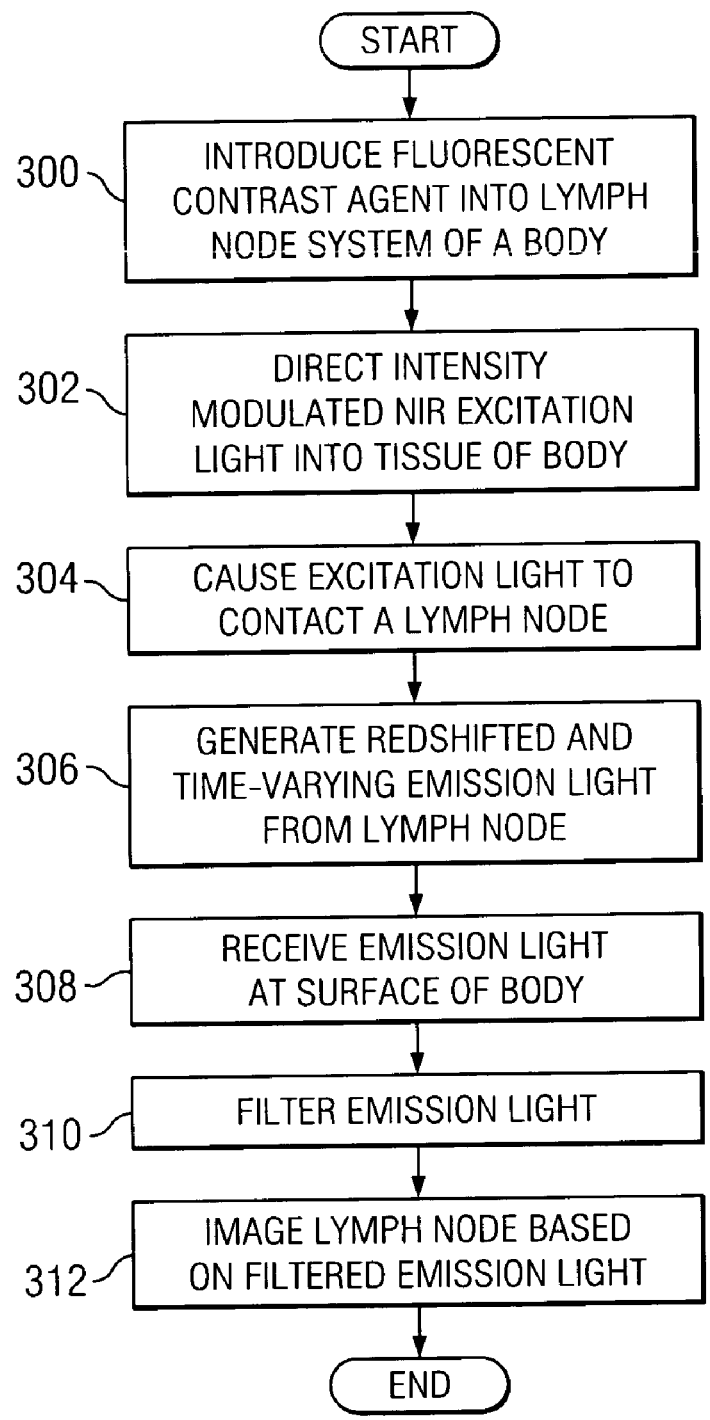
FIG. 3 is a flowchart illustrating a method for detecting lymph nodes according to one embodiment of the present invention.

FIG. 3 is a flowchart illustrating an example method for detecting lymph nodes according to one embodiment of the present invention. The example method begins at step 300 where a fluorescent contrast agent is administered to the patient and introduced into a lymphatic system of a body of a human. Any suitable fluorescent contrast agent may be utilized; however, a preferred fluorescent contrast agent is indocyanine green ("ICG") and its derivatives. ICG is a compound with FDA approval for systemic administration in humans. In one embodiment, ICG is excited at 780 nm and emits at 830 nm, has an extinction coefficient of 130,000 $M^{-1}$ $cm^{-1}$, a fluorescent lifetime of 0.56 ns and a quantum efficiency of 0.016 for the 780/830 nm excitation/emission wavelengths. At step 302, intensity modulated NIR excitation light is directed into the tissue of the body. In one embodiment, the NIR excitation light has a wavelength between approximately 700 and 900 nm. Any suitable modulation frequency may be utilized for the intensity modulated NIR excitation light; however, in one embodiment, the modulation frequency is approximately 100 MHz.

The excitation light is caused to contact a node of the lymphatic system, as denoted by step 304. In one embodiment, a sentinel lymph node is contacted. This generates a red shifted and time-varying emission light from the lymph node, as denoted by step 306. This generated emission light propagates through the tissue to the surface of the body where it is received, as denoted by step 308. The emission light is then collected and passed through one or more optical filters that are selected to reject the excitation portion of the re-emitted light signal, as denoted by step 310. The detected fluorescence wave is both phase shifted by θ and AC amplitude attenuated relative to the incident excitation light because of both the propagation of excitation and emission light within the tissue as well as the relaxation kinetics of the fluorophore. The lymph node may then be imaged based on the filtered emission light, as denoted by step 312, which then ends the example method in FIG. 3.

Figure 4A:
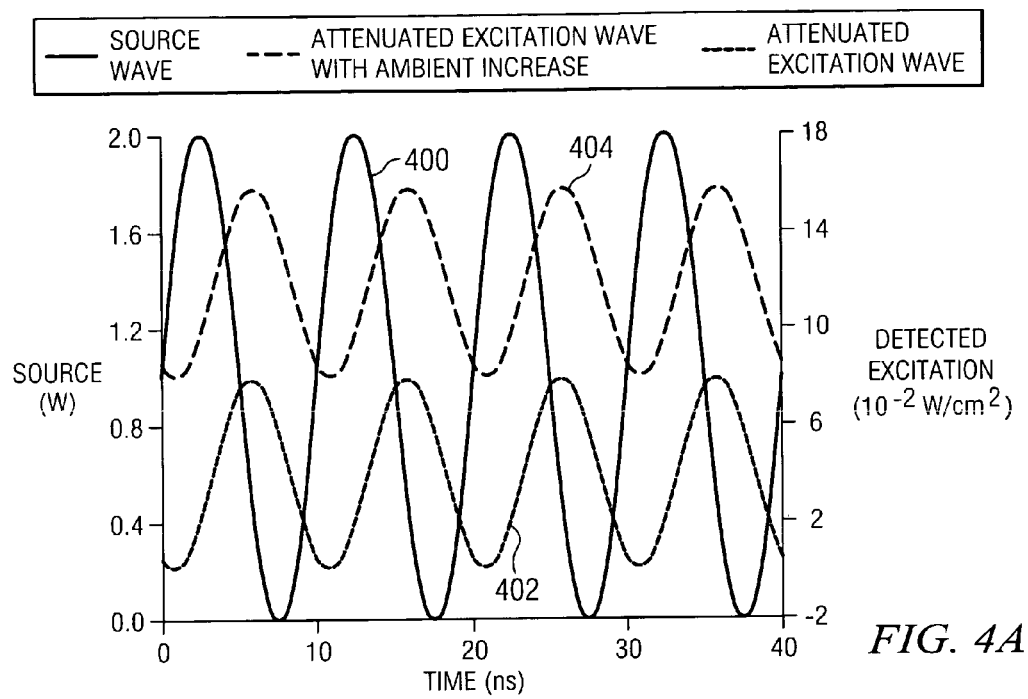
FIGS. 4A and 4B are schematics illustrating the nominal intensity values of an incident modulated excitation wave, the generated emission wave that propagates to the surface and the amplitude in the measured wave if ambient, nonmodulated light were also collected.
Figure 4B:
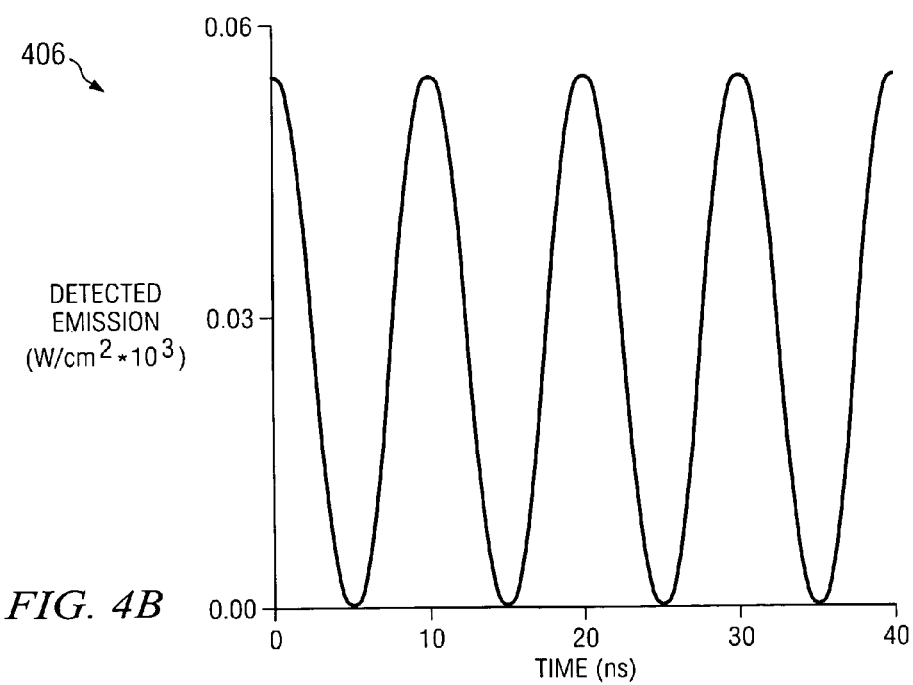

FIGS. 4A and 4B are schematics illustrating the nominal intensity values of an incident modulated excitation wave, the generated emission and excitation waves that propagate to the surface, and the amplitude in the measured excitation wave if ambient, non-modulated light were also collected according to an embodiment of the present invention. Unlike continuous wave techniques, the contribution of background light to the detected fluorescent signal is eliminated from the AC and θ components because of the inherent filtering of non-modulated light using FDPM. This rejection of non-modulated light through FDPM techniques results in a reduction of the measurement noise floor, enabling greater penetration depth into the tissue and more sensitive detection of fluorescent targets. However, as with continuous wave techniques, inadvertent collection of propagated excitation light increases the measurement noise floor and reduces sensitivity and depth of penetration.

With reference to FIGS. 4A and 4B, a snapshot of an intensity modulated (100 MHz) excitation light 400 and an attenuated excitation wave 402 detected at a distance of approximately two centimeters from the source is illustrated. The scattering properties of the solution are $\mu_s'=10$ $cm^{-1}$ and $\mu_a d=0.1$ $cm^{-1}$. If there is a change in the ambient light levels, the DC amplitude (or average) of the detected signal is affected, whereas the AC amplitude is not, demonstrated by a second AC wave 404. Consequently, FDPM detection involves a frequency filter, which collects only that light that is intensity modulated and therefore rejects non-modulated ambient light, as described above. The modulated fluorescent light (shown by a call-out 406) detected two centimeters away from an excited fluorophore region of micromolar concentration is additionally attenuated from the source with a reduced signal of the order of approximately $10^{-4}$. The changing levels of ambient light, or the average of the modulated signal (termed the DC component), will not affect modulated fluorescence amplitude. Rejection of modulated excitation light (as well as ambient light) is accomplished via appropriate selection of optical filters.

Figure 5:
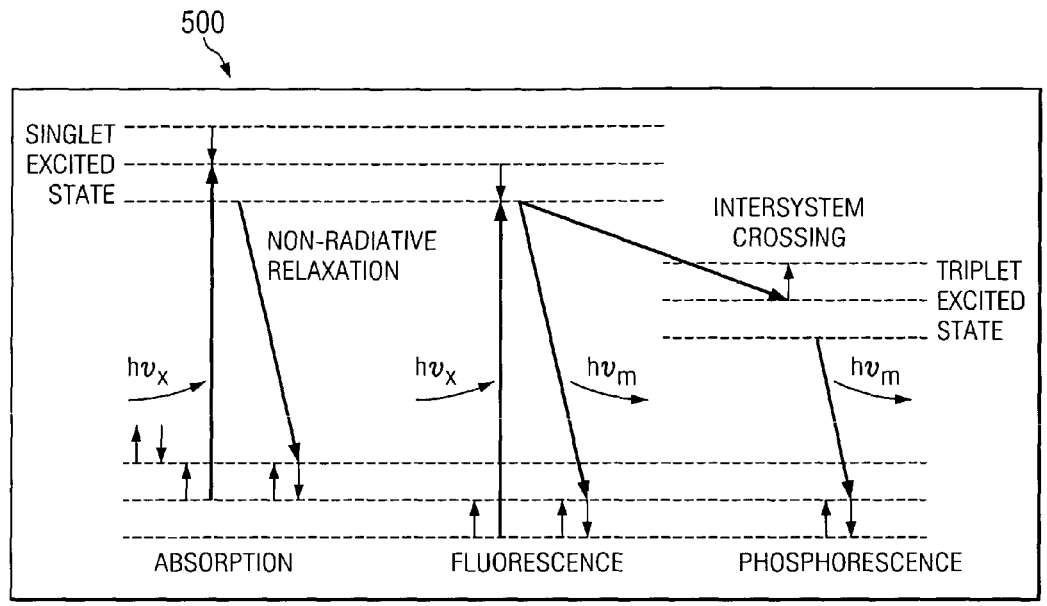
FIG. 5 is a Jablonski diagram illustrating radiative and non-radiative relaxation of fluorophores to the ground state according to an embodiment of the invention.

FIG. 5 is the well known Jablonski diagram 500 illustrating radiative and non-radiative relaxation of fluorophores to the ground state according to an embodiment of the invention. As described above, ICG is one example of a fluorescent contrast agent that may be utilized within the teachings of the present invention. ICG has been employed as a contrast agent for surface and sub-surface disease detection in small animal studies. Others have shown through immunohistochemical staining that targeted delivery of the fluorophore in the digestive tract could enable novel endoscopic detection of small cancers. Upon injecting ICG bound to purified lipoprotein into the subarachnoid space of the neonatal rat, a cooled CCD camera has been used to detect the fluorescence in the subarachnoid space and cerebrospinal fluid pathways in vivo. The peptide transferrin has been coupled to indotricarbocyanine in order to facilitate cellular uptake and internalization into tumor cells overexpressing the transferrin receptor. More recently, some researchers have compared the retention of ICG and its derivatized analogue, cypate, with the receptor-specific peptide-cypate conjugate (cytate) in a rat tumor model. They showed that receptor-mediated uptake results in as much as a 17:1 tumor:muscle fluorescence contrast using imaging techniques.

A fluorescent dye may be made lifetime-sensitive to its environment. When the dyes are conjugated tightly together within a complex, an activated fluorophore can be quenched or can relax non-radiatively by directly transferring its energy to a neighboring dye molecule, as shown in FIG. 5. The net result is that the mean lifetime τ of the excited singlet state of the fluorophore can be comparatively lengthened when compared to the fluorophore, which is free and distant from its neighboring dye molecules. Certainly, other paradigms for lifetime-sensitive fluorescent contrast agents may be envisioned, but they may require quantification of the fluorescent decay kinetics from re-emitted multiply scattered light. As the lifetime of the fluorescent dyes changes, the AC and the θ changes, enabling "reporting" of an "activated" dye.

Figure 6:
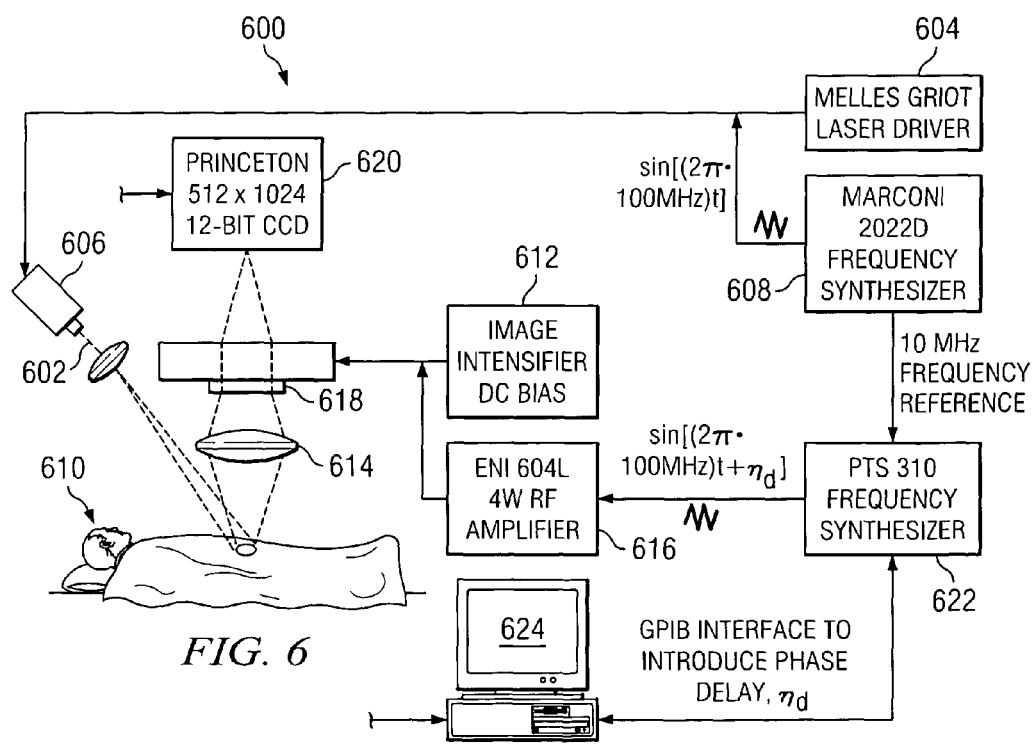
FIG. 6 is a schematic illustrating a system for excitation area illumination and area detection using frequency-domain photon migration ("FDPM") measurements according to an embodiment of the present invention.

FIG. 6 is a schematic of an example FDPM system 600 for use in imaging lymph nodes according to an embodiment of the present invention. As described above, other suitable imaging techniques may be utilized, such as the techniques described in U.S. Pat. No. 5,865,754. FIG. 6 illustrates FDPM system 600 being utilized for imaging a target body within a human. The present invention contemplates more, less, or different components than those shown in system 600 of FIG. 6. In the illustrated embodiment, system 600 includes an intensity modulated light source 602 with a laser driver 604, operatively coupled to a laser diode 606 and reference frequency generator 608. Light source 602 is configured to deliver intensity modulated excitation light into tissue of a body 610. The re-emitted light from body 610 is focused onto a gain modulated image intensifier 612 by a lens 614.

In one embodiment, image intensifier 612 includes a photocathode face that converts photons to electrons, a multi-channel plate ("MCP") that multiplies the electronic signal by avalanche multiplication, and a phosphorescent screen that converts electrons into an optical image. Preferably, image intensifier 612 is a fast intensifier of the variety manufactured by Litton Electronics, Inc., which enables modulation by applying a DC bias and an RF signal from an amplifier 616 between the photocathode and the MCP; however, other suitable image intensifiers may be utilized. In this example, the intensity modulation of the image from image intensifier 612 is phase-locked to laser diode 606 by a 10 MHz output signal from generator 608. By modulating laser diode 606 and image intensifier 612 at the same frequency, a steady-state image results on the phosphor screen. The image from the phosphor screen is focused through an interference filter 618 on a charge coupled device ("CCD") camera 620 by lens 614. Camera 620, in the illustrated embodiment, has a 512×512 array of CCD detectors configured to provide a corresponding pixelated image. Camera 620 may be operatively coupled to any suitable processor in order to image the lymph node of body 610.

In operation, following each acquired image, a phase delay between image intensifier 612 and laser diode 606 is induced by stepping the phase of image intensifier 612 to values between 0 and 360° with a frequency synthesizer 622 under the control of a suitable processor. Since the gain modulation of image intensifier 612 and laser diode 606 occurs at the same frequency, homodyning results in a steady phosphorescent image on image intensifier 612, which is dependent upon phase. Preferably, control between synthesizer 622 and the processor is obtained by a conventional general purpose interface bus ("GPIB") 624; however, other suitable interfaces may be utilized. Images from the phosphorescent screen image intensifier 612 may then be gathered at each phase delay by CCD camera 620. Incremental phase delayed images are then used to generate a map of phase-shift in intensity modulation ratio between the excitation and re-emitted light from body 610. By applying interference or suitable optical filters, the emission light may be selectively separated from the excitation light and measured. Camera 620 output may be processed by any suitable processor. Optical filters 618 may be any suitable optical filters, such as a band pass filter, a long pass filter, a holographic notch filter, or any combination thereof, or any optical scheme to reject excitation enabling registration of the fluorescent signal.

In one embodiment, a gain-modulated image intensifier as a homodyned, multi-pixel radio frequency phase-sensitive camera was employed. The use of a gain-modulated image intensified charge-coupled camera (ICCD) was applied to FDPM imaging of absorbing in scattering phantoms. Essentially, instead of detecting the light that has propagated to a point or series of points on the tissue surface, the ICCD system acts as an area detector, collecting the spatially distributed light re-emitted from the tissue surface. In one embodiment, the mammary chain was scanned using the ICCD area detector to collect the emitted fluorescence owing to ICG. Excitation was accomplished by illuminating the tissue surface with a 4 cm diameter expanded beam of a 20 mW, 780 nm laser that was modulated at 100 MHz. Test results in phantom studies are described below.

FIGS. 7A through 7D illustrate the DC (a.u.) and AC (a.u.) contrast images (background subtracted) that were simultaneously obtained when a 100 μL target containing 100 fmol of ICG was positioned at increasing depths within one percent of a Liposyn® in increments of one centimeter from an illumination surface, using the system of FIG. 6. The Liposyn® was used to mimic the optical properties of tissue. The images were obtained by subtracting the corresponding absence image taken under identical measurement conditions in order to eliminate excitation light leakage through the optical filters. Both DC and AC images track the position of the fluorescent target (when detected) as its depth (z) is moved within the planar (x-y) field of view. A long pass and band pass filter combination was used for optical filters 618 (FIG. 6) in these studies at each target depth and the integration time was varied between 200 and 700 ms because the amount of light collected at the image intensifier photocathode varied. Consequently, the units of AC and DC cannot be directly compared at different target depths. The results show that as the distance of the target position becomes greater than one centimeter from the tissue surface, the DC (continuous wave) signal is lost, whereas sufficient signal is evident in AC measurements as deep as three centimeters. These results indicate reduced noise floor of AC over DC measurements and the impact upon detecting smaller amounts of fluorophore at greater tissue depths.

Figure 7A:
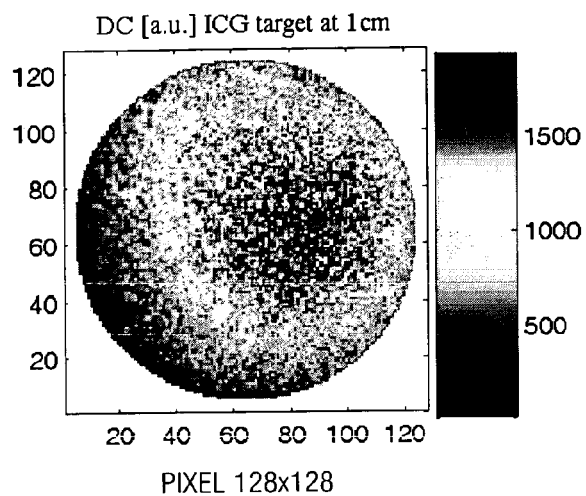
FIGS. 7A through 7D are DC and AC (a.u.) contrast images (background subtracted) that were simultaneously obtained when a 100 μL target containing 100 fmol of ICG was positioned at increasing depths within 1% Liposyn® in increments of 1 cm from the illumination surface.
Figure 7B:
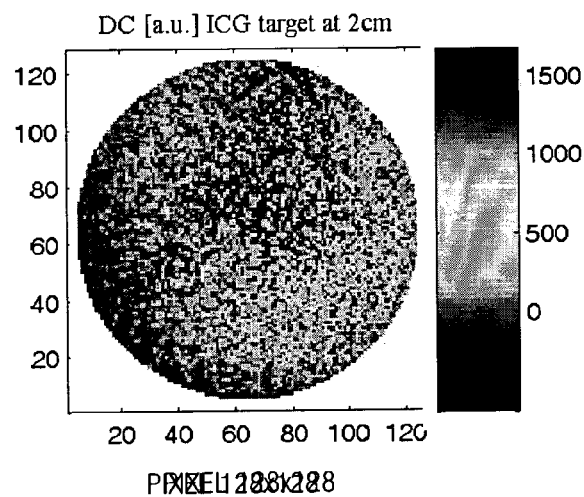
Figure 7C:
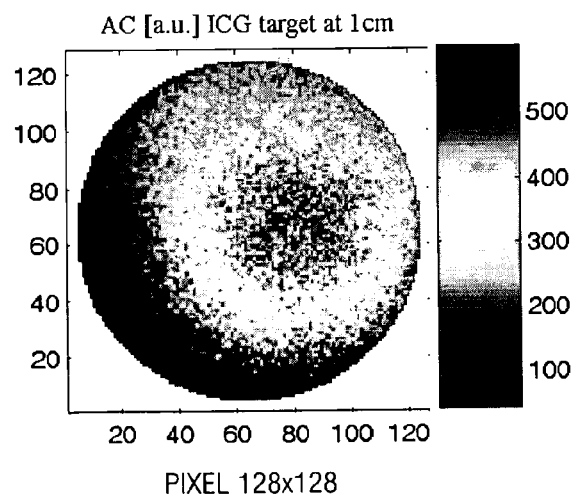
Figure 7D:
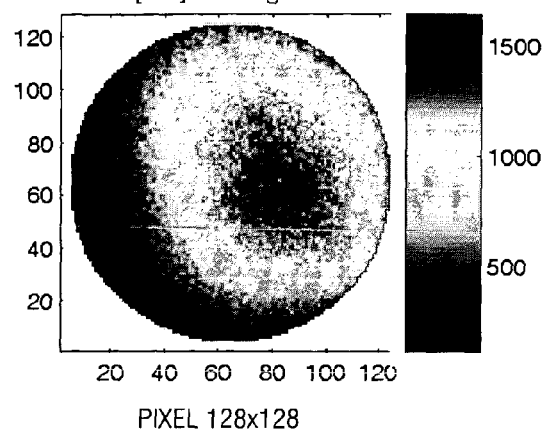
Figure 8A:
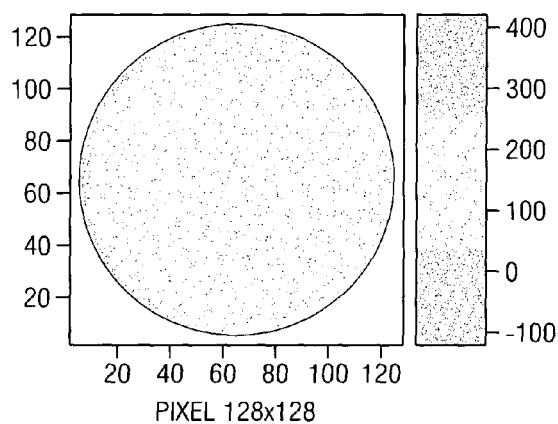
FIGS. 8A and 8B are DC (a.u.) and AC (a.u.) images, respectively, of the phantom scattering surface with no fluorescent target present.
Figure 8B:
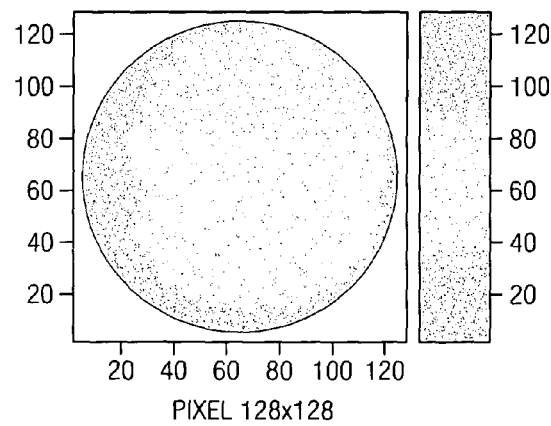

FIGS. 8A and 8B illustrate the image of a noise floor owing to excitation light gauge for both DC and AC images with identical settings and processing as that in FIG. 7C, with the exception that the fluorescent target was not present in the body. The mean and standard deviation of the DC intensity counts were approximately 83 and 130 (a.u.) whereas those of the AC intensity counts were 48 and 17 (a.u.), below the AC contrast value in FIG. 7C. These numbers are consistent with a lower noise floor associated with FDPM over continuous wave measurements.

Thus, as shown above, excitation light rejection is a significant barrier for the detection of increasing target depths. Consequently, reduction of the noise floor through reduction of excitation light leakage is important for increased penetration depth of fluorescence enhanced optical imaging. Fluorescence enhanced NIR optical imaging measurements provide localization comparable with lymphoscintigrams at tissue depths up to three centimeters for targets as small as five millimeters. With the developing chemistry of targeted fluorescent contrast agents, fluorescence enhanced optical imaging may have added benefit to sentinel lymph node mapping if NIR excitable contrast agents could not only locate sentinel lymph nodes but also report if cancer cells are present within the node.

Experimental depth sensitivity studies and corresponding results are also illustrated in U.S. Provisional Patent Application No. 60/395,279, filed Jul. 12, 2002, which is herein incorporated by reference for all purposes.

Although embodiments of the invention and their advantages are described in detail, a person skilled in the art could make various alterations, additions, and omissions without departing from the spirit and scope of the present invention, as defined by the appended claims.

What is claimed is:

1. Method for detecting lymph nodes in a human, comprising:
   introducing a fluorescent contrast agent into a lymphatic system of a body;
   directing time-varying excitation light into the tissue of the body;
   causing the time-varying excitation light to contact a lymph node of the lymphatic system, whereby a time-varying emission light is generated, wherein the generated time-varying excitation light comprises a spatial distribution selected from the group consisting of a planar wave, a series of lines of illumination, concentric circles of illumination, and a ronchi rule pattern;
   detecting the time-varying emission light at a surface of the body;
   using frequency-domain photon migration, filtering light that is not time-varying;
   filtering the time-varying emission light to reject excitation light re-emitted from the lymph node; and
   imaging the lymph node of the lymphatic system.

2. The method of claim 1, wherein introducing the fluorescent contrast agent comprises introducing indocyanine green ("ICG").

3. The method of claim 1, wherein directing time-varying excitation light into the tissue of the body comprises directing time-varying excitation light into the tissue of the body with a light source selected from the group consisting of a pulse, a series of pulses, pseudo random modulation, sinusoidally modulated light, and a square wave.

4. The method of claim 1, wherein the spatial distribution is the ronchi rule pattern.

5. The method of claim 1, further comprising modulating the excitation light to obtain a wavelength between approximately 700 nm and 900 nm.

6. The method of claim 1, wherein causing the excitation light to contact a lymph node of the lymphatic system comprises causing the excitation light to contact a sentinel lymph node of the lymphatic system.

7. A system for detecting lymph nodes in a human, comprising:
   a laser diode operable to direct time-varying near-infrared excitation light into the tissue of a body;
   one or more optical components adapted to provide the time-varying near-infrared excitation light a spatial distribution selected from the group consisting of a planar wave, a series of lines of illumination, concentric circles of illumination, and a ronchi rule pattern;
   an image intensifier operable to detect, at a surface of the body, a redshifted and time-varying emission light generated by the near-infrared time-varying excitation light contacting a lymph node of the lymphatic system;
   one or more optical filters operable to reject excitation light re-emitted from the lymph node; and
   an imaging apparatus operable to image the lymph node of the lymphatic system.

8. The system of claim 7, further comprising a fluorescent contrast agent adapted to be injected into a lymphatic system of a body, the fluorescent contrast agent selected from the group consisting of a non-specific fluorescent contrast agent and a specific fluorescent contrast agent.

9. The system of claim 7, wherein the spatial distribution is the ronchi rule pattern.

10. The system of claim 7, further comprising a frequency generator to modulate the near-infrared time-varying excitation light to obtain a wavelength between approximately 700 nm and 900 nm.

11. The system of claim 7, wherein the one or more optical filters are selected from the group consisting of a band pass filter, a long pass filter, and a holographic notch filter.

12. The system of claim 7, wherein the one or more optical filters comprises any combination of the following filters: a band pass filter, a long pass filter, and a holographic notch filter.

13. The system of claim 7, wherein the lymph node of the lymphatic system comprises a sentinel lymph node.

14. The system of claim 7, wherein the imaging apparatus is a charge coupled device camera.

15. A method for detecting lymph nodes in a human, comprising:
   introducing a fluorescent contrast agent into a lymphatic system of a body;
   directing into the tissue of the body near-infrared time-varying excitation light modulated to obtain a wavelength between approximately 700 nm and 900 nm;
   causing the near-infrared time-varying excitation light to contact a sentinel lymph node of the lymphatic system, whereby a redshifted and time-varying emission light is generated;
   detecting the generated time-varying emission light at a surface of the body;
   optically filtering the generated time-varying emission light to reject excitation light re-emitted from the sentinel lymph node;
   quantitizing a fluorescence characteristic throughout at least a portion of the sentinel lymph node from the generated time-varying emission light by establishing a number of values with a processor, each of the values corresponding to a level of the fluorescence characteristic at a different position within the sentinel lymph node, the level of the fluorescence characteristic varying with a composition of the sentinel lymph node; and
   imaging the sentinel lymph node in accordance with the values.

16. The method of claim 15, wherein introducing the fluorescent contrast agent comprises introducing indocyanine green ("ICG").

17. The method of claim 15, wherein directing into the tissue of the body near-infrared time-varying excitation light comprises directing into the tissue of the body time-varying excitation light with a light source selected from the group consisting of a pulse, a series of pulses, pseudo random modulation, sinusoidally modulated light, and a square wave.

18. The method of claim 15, wherein the fluorescence characteristic corresponds to at least one of fluorescence lifetime, fluorescence quantum efficiency, fluorescence yield, and fluorescence uptake.

19. The method of claim 15, wherein quantitizing a fluorescence characteristic further comprises determining the values from a mathematical relationship modeling light scattering behavior of the portion of the sentinel lymph node.

20. The method of claim 19, wherein the mathematical relationship corresponds to a diffusion equation approximation of multiply scattered light.

21. A method of lymph node analysis of humans, comprising:
   exposing a lymph node to an excitation light with a predetermined time varying intensity, the lymph node multiply scattering the excitation light;
   detecting a multiply scattered light emission from the lymph node in response to said exposing;
   determining a number of values from the emission with a processor, the values each corresponding to a level of a fluorescence characteristic at a different position within the lymph node, the level of the characteristic varying with lymph node composition; and
   generating an image of lymph node compositional variation in accordance with the values.

22. The method of claim 21, wherein exposing the lymph node to an excitation light comprises exposing the lymph node to a near-infrared time-varying excitation light.

23. The method of claim 21, wherein the fluorescence characteristic corresponds to at least one of fluorescence lifetime, fluorescence quantum efficiency, fluorescence yield, and fluorescence uptake.

* * * * *